United States Patent [19]

Weyl et al.

[11] Patent Number: 5,246,562
[45] Date of Patent: Sep. 21, 1993

[54] GAS MEASUREMENT SENSOR, ESPECIALLY FOR DETERMINING OXYGEN CONCENTRATION IN EXHAUST GASES OF INTERNAL COMBUSTION ENGINES

[75] Inventors: Helmut Weyl, Schwieberdingen; Romuald Fries, Ditzingen-Heimerdingen, both of Fed. Rep. of Germany

[73] Assignee: Robert Bosch GmbH, Stuttgart, Fed. Rep. of Germany

[21] Appl. No.: 862,580

[22] PCT Filed: Sep. 18, 1991

[86] PCT No.: PCT/DE91/00739
§ 371 Date: Jun. 24, 1992
§ 102(e) Date: Jun. 24, 1992

[87] PCT Pub. No.: WO92/08127
PCT Pub. Date: May 14, 1992

[30] Foreign Application Priority Data

Oct. 26, 1990 [DE] Fed. Rep. of Germany ....... 4034072
Aug. 9, 1991 [DE] Fed. Rep. of Germany ....... 4126378

[51] Int. Cl.⁵ ............................................. G01N 27/26
[52] U.S. Cl. .................................. 204/424; 204/426; 204/428
[58] Field of Search ............... 204/421, 424, 425, 426, 204/427, 428, 429

[56] References Cited

U.S. PATENT DOCUMENTS

| | | | |
|---|---|---|---|
| 4,141,813 | 2/1979 | Kita et al. | 204/428 |
| 4,187,163 | 2/1980 | Steinke et al. | 204/428 |
| 4,282,080 | 8/1981 | Müller et al. | 204/426 |
| 4,283,261 | 8/1981 | Maurer et al. | 204/426 |
| 4,294,679 | 10/1981 | Maurer et al. | 204/426 |
| 4,307,373 | 12/1981 | Johnston | 338/34 |
| 4,502,939 | 3/1985 | Holfelder et al. | 204/429 |
| 4,588,494 | 5/1986 | Kato et al. | 204/426 |
| 4,732,663 | 3/1988 | Kato et al. | 204/426 |
| 4,786,399 | 11/1988 | Wertheimer et al. | 204/427 |
| 4,818,363 | 4/1989 | Bayha et al. | 204/426 |

FOREIGN PATENT DOCUMENTS 0415007 3/1991 European Pat. Off. .
2908916 9/1980 Fed. Rep. of Germany .

Primary Examiner—John Niebling
Assistant Examiner—Bruce F. Bell
Attorney, Agent, or Firm—Frishauf, Holtz, Goodman & Woodward

[57] ABSTRACT

A gas measurement sensor (10) which sealingly encloses an axially oriented sensor (27) having an elongated, planar shape in the longitudinal bore (19) of its metal housing (11); while the section (27/1) on the gas measuring side of the sensor (27) has at least one sensor element (38) and possibly heating elements, the end section (27/3) on the connecting side is provided with layered contact surfaces (36), which are in contact with the sensor elements (38)/heating elements via strip conductors (37). A connector plug (43) surrounding the sensor (27) on the connecting side consists of a contact element support (44), an opposite wall (45), contact elements (46) and an annularly-shaped spring element (47); because of its mechanical pre-stressing, the spring element (47) presses the contact elements (46) of the contact element support (44) and of the opposite wall (45) against the contact surfaces (36) of the sensor (27). On the connecting side the contact elements (46) have connecting points (56) for connecting conductors (57). The connector plug (43) allows the installation on the sensor element (27) without damage to the sensor contact surfaces (36) and possible coatings on connector plug contact elements (46).

19 Claims, 6 Drawing Sheets

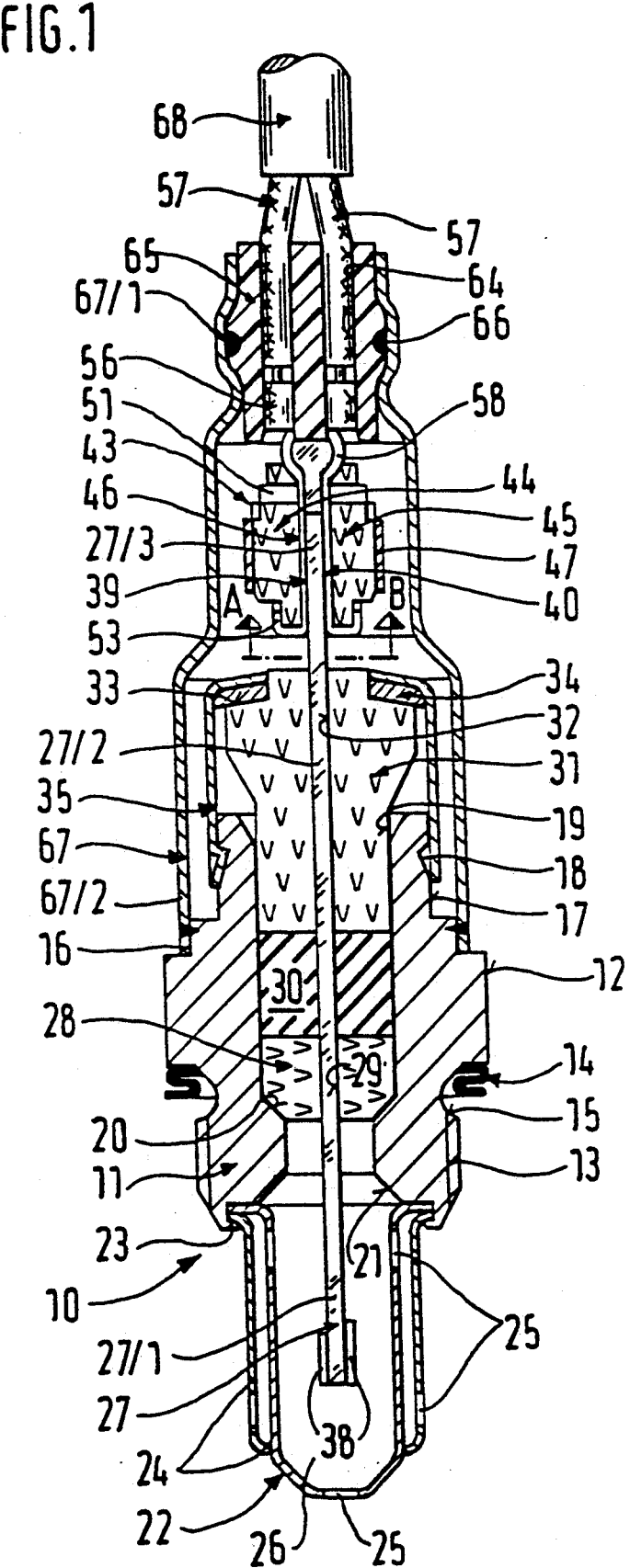

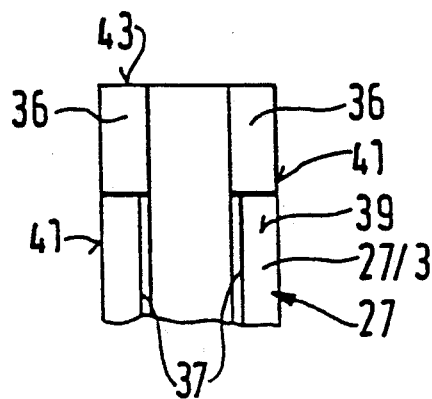
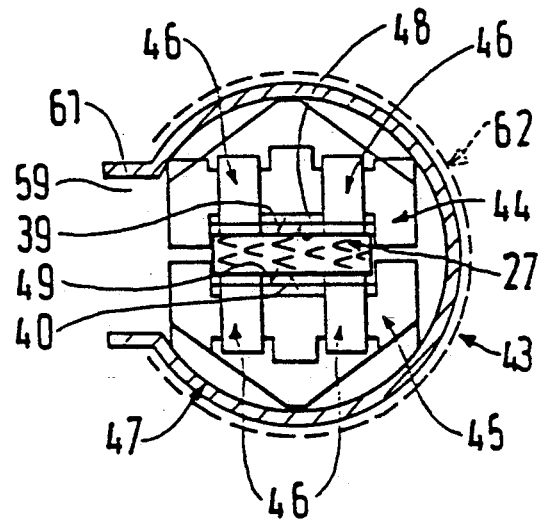
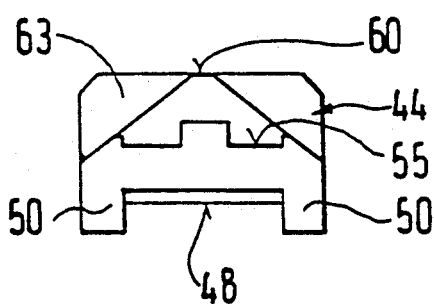
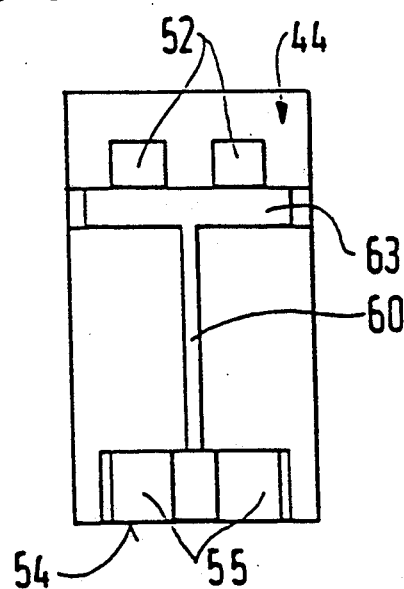

ns sensor

GAS MEASUREMENT SENSOR, ESPECIALLY FOR DETERMINING OXYGEN CONCENTRATION IN EXHAUST GASES OF INTERNAL COMBUSTION ENGINES

BACKGROUND OF THE INVENTION

The invention relates to a gas measurement sensor. In the gas measurement sensor in accordance with the species known from EP 0 087 626 B1 (FIGS. 4 to 6), corresponding to Bayha and Weyl/Bosch U.S. Pat. No. 4,818,363, its elongated planar sensor element has thin contact surfaces made of a platinum metal in its section on the connecting side; when this section on the connecting side of the sensor element is inserted into the connector plug on the connecting side, which presses with metallic spring elements, which are mechanically pre-stressed and are used as opposite contacts, on the contact surfaces of the sensor element or of a possible layered heating element, these contact surfaces can be damaged and false indications or false control actions can be caused because of these damages. If such contact surfaces of sensor elements or spring elements of the connector plug are provided with a thin, corrosion-resistant coating (for example of gold), these contact surfaces and coatings can already be damaged or destroyed when the sensor element and connector plug are plugged together and thus can impair the perfect function of the gas measurement sensor.

Advantages of the Invention

In contrast thereto the gas measurement sensor in accordance with the present invention has the advantage that in the course of the assembly of the sensor element and the connector plug on the connecting side, neither the contact surfaces of the sensor element nor possible corrosion-resistant coatings on the contact elements are damaged and that therefore impairment of the gas measurement sensor in this section is prevented to the greatest extent.

A further advantage is seen in that the individual elements involved in the contact operations of the connector plug on the connecting side with the planar sensor element can be easily produced and assembled.

Advantageous further embodiments and improvements of the gas measurement sensor recited in the main claim are possible by means of the steps recited in the dependent claims; this is particularly applicable for connector plugs of such gas measurement sensors which have, on at least one of the two large areas of the sensor, contact surfaces of sufficiently large size and where the distances between the contact surfaces of the sensor and between the contact elements of the connector plug are still sufficiently large and thus assured.

BRIEF DESCRIPTION OF THE DRAWINGS

An exemplary embodiment of the invention is illustrated in the drawings and explained in detail in the description below.

Shown are in FIG. 1 a longitudinal section through a gas measurement sensor of the invention shown in an enlargement, FIG. 2 an enlarged top view of a large area containing two contact surfaces of an end section on the connecting side of an elongated, planar sensor, FIG. 3 an enlarged view in the direction A/B (turned by 90 degrees) of the connector plug contained in the gas measurement sensor of FIG. 1, FIG. 4 a view of a contact element support in the direction towards the connecting side of the connector plug in accordance with FIG. 3, FIG. 5 a top view on the back, pointing away from the sensor, of the contact element support in accordance with FIG. 4, FIG. 6 an enlarged top view of a large area containing three contact surfaces of a sensor for the connector plug in accordance with FIG. 7, FIG. 7 an enlarged longitudinal section through a connector plug which is provided for planar sensors with up to three contact surfaces per large side (see section line VII—VII in FIG. 9), FIG. 8 an enlarged top view of the front side, provided with contact elements, of a contact element support (or an opposite wall) of the connector plug in accordance with FIG. 7, and FIG. 9 a cross section through the connector plug along the line IX—IX of FIG. 7.

DESCRIPTION OF THE EXEMPLARY EMBODIMENTS

Figure 6:
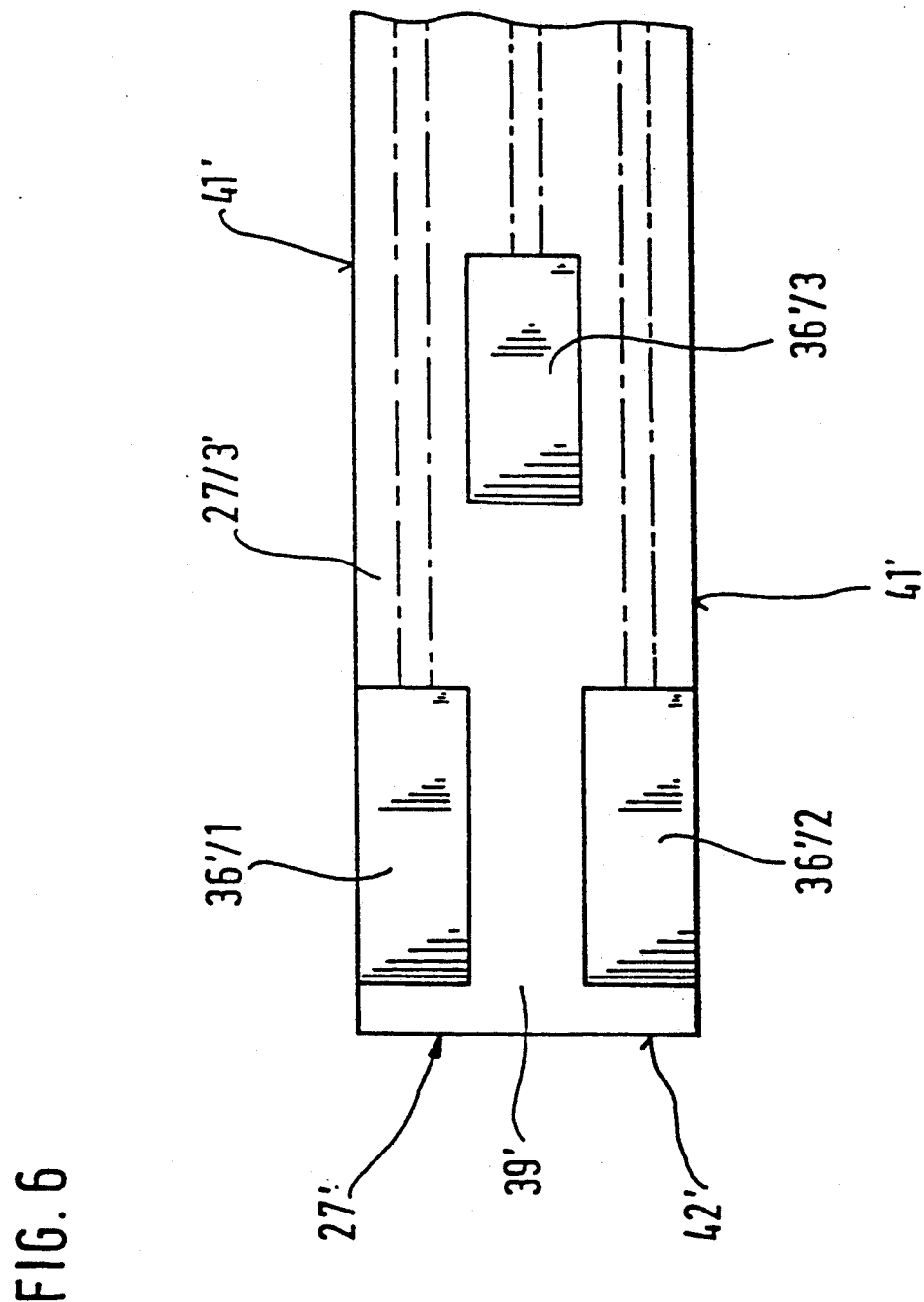

The gas measurement sensor 10 shown in FIG. 1 has a pipe-shaped metal housing 11 which has on its exterior a hexagonal wrench fitting 12 and a screw thread 13 as means for installing the gas measurement sensor 10 into a gas measurement line, not shown; a seal ring 14, captively seated in an annular groove 15 disposed between the hexagonal wrench fitting 12 and the screw thread 13, is used for the sealed installation of this metal housing 11. A coaxially first longitudinal section 16 of a smaller diameter is formed on the metal housing 11 on the connecting side of the hexagonal wrench fitting 12, and a second longitudinal section 17, which has an even more reduced diameter, follows this first longitudinal section 16 on the connecting side; this second longitudinal section 17 of the metal housing 11 is provided with an annular groove 18 on its exterior.

The metal housing 11 has a longitudinal bore 19 with a coaxial shoulder 20, which faces away from the gas measuring side of the gas measurement sensor; on the gas measuring side the end section of this longitudinal bore 19 is widened into a bored out part 21.

A protective pipe 22 is fixed in the bored out part 21 of the longitudinal bore 19 of the metal housing 11 by means of a flange 23. In its so-called double casing 24 this protective pipe 22 has a number of inlet and outlet openings 25 for the gas to be measured; the space enclosed by the protective pipe 22 is the measuring chamber 26 of the gas measurement sensor 10.

The section 27/1 on the gas measuring side of a sensor 27 extends at a distance from the protective pipe 22 into this measuring chamber 26; this sensor 27 has an elongated planar shape and extends through the longitudinal bore 19 of the metal housing 11. This sensor 27 is supported in an electrically insulated manner in the longitudinal bore 19 of the metal housing 11:

To support the sensor 27 in the longitudinal bore 19 of the metal housing 11, there are used a first electrically insulating ceramic element 28, which rests on the gas measuring side on the shoulder 20 of the longitudinal bore 19 of the metal housing and has a longitudinal channel 29 for the lateral guidance of the sensor 27, then a package-like seal 30 which adjoins the first ceramic element 28 on the connecting side and encloses the sensor 27 and extends as far as the wall of the longitudinal bore 19 of the metal housing 11 and consists of an electrically insulating material, for example soapstone, and then additionally of a second electrically insulating ceramic element 31, which also adjoins the seal 30 on the connecting side, fills the cross section of the longitudinal bore 19 of the metal housing 11, has a longitudinal channel 32 for the lateral fixing of the sensor 27 and extends out of the longitudinal bore 19 of the metal housing 11 at the connecting side; the section towards the connecting side of the second ceramic element 31 is preferably enlarged in its diameter in the shape of a head and has a coaxial annular shoulder 33 on the connecting side. A plate spring 34 which is mechanically pre-stressed rests on this shoulder 33 of the second ceramic element 31, which presses this ceramic element 31, the seal 30 and the first ceramic element 28 against the shoulder 20 in the longitudinal bore 19 of the metal housing 11; possibly a seal ring (not shown) can also be disposed between the shoulder 20 in the longitudinal bore 19 of the metal housing 11 and the first ceramic element 28. A pipe-shape fastening cap 35, the end section on the gas measuring side of which is fixed in a known manner in the annular groove 18 of the second longitudinal section 17 on the exterior of the metal housing 11, is used as support resting on the periphery of the plate spring 34.

The section of the sensor 27 extending out of the seal 30 on the connecting side is identified as the section 27/2 on the connecting side and extends with its end section 27/3 on the connecting side out of the second ceramic element 31. Two contact surfaces 36 are disposed on this end section 27/3 on the connecting side of the sensor 27—as shown in FIG. 2—, which consist of an electrically conductive, corrosion-resistant material, such as platinum or gold, and which are connected by means of strip conductors 37 with at least one sensor element 38 or with a (not shown) heating element, temperature sensor or the like, located on the gas measuring section 27/1 of the sensor 27; in a preferred manner these two contact surfaces 36 are applied on at least one of the two large areas 39, 40 of the sensor 27 by means of known methods (for example screen printing) and from known materials (for example platinum). The short sides extending along the sensor 27 are identified with 41 and the narrow front face on the connecting side with 42 (not shown). - The sensor element 38, which is only suggested in FIG. 1, can have various functions (see, for example, DE 29 28 496 C2, DE 30 17 947 C2, DE 28 26 515 C2, DE 28 55 012 A1, DE 29 09 452 C2, DE 29 08 916 C2); the disclosures of the above mentioned references are a part of the present description.

A connector plug 43 is pushed on the end section 27/3 on the connecting side having the contact surfaces 36 (in FIG. 2) of the sensor 27 (see FIG. 3). This connector plug 43 consists of an contact element support 44, an opposite wall 45 to the contact element support 44, contact elements 46 and a spring element 47. The contact element support 44 and the opposite wall 45 are electrically insulating components of ceramic material and each one of their fronts 48 or 49 faces a large area 39 or 40 of the sensor 27 and is arranged parallel to it; the contact element 44 and the opposite wall 45 of the connector plug 43 are at a distance from each other. Guide bars 50 are formed on the front 48 of the contact element support 44 (see FIG. 4), between which the end section 27/3 on the connecting side of the sensor 27 is fixed with its two short sides 41. In this exemplary embodiment, two contact elements 46, which are made of strip-shaped sheet metal and are fixed on the contact element support 44 extend on the front 48 of the contact element support 44 in the longitudinal direction; for fixing each contact element 46 it is possible, for example, to use finger-shaped sections 51 of sheet metal formed on the contact element 46, which can be anchored in channels 52 of the contact element support 44 (see FIGS. 1 and 5). The end sections 53 on the gas measuring side of the two contact elements 46 are bent around the front face 54 on the gas measuring side of the contact element support 44 as far as the back 55 of the contact element support 44. On the connecting side each of the contact elements 46 are extended strip-like and embodied at this end section as connecting points 56 for connecting conductors 57; the connecting points 56 are embodied in this exemplary embodiment as sleeves (not shown) with longitudinal slits. A bulge 58 of the areas of each contact element 46, located between the connecting elements 56 and the connecting element support 44, can be useful for length compensation in case of heat expansion. The contact elements 46 are provided with an electrically well-conducting, corrosion-resistant coating (not shown)(for example of gold) which, however, is only a few μm thick.

The opposite wall 45, which for practical reasons should be of the same configuration as the contact element support 44, rests on the second large area 40 of the end section 27/3 on the connecting side of the sensor 27. In the exemplary embodiment shown, this opposite wall 45 is also provided with contact elements 46, which are disposed by means of contact surfaces 36 on the second large area 40 of the end section 27/3 on the connecting side of the sensor 27; in the case where no contact surfaces 36 are present on the second large area 40 of the sensor 27, the contact elements 46 can of course be omitted.

The contact element support 44, the opposite wall 45 and the end section 27/3 on the connecting side of the sensor 27 disposed between them are together enclosed by an annularly-shaped spring element 47 and kept together; in its peripheral extension this spring element 47 has an interruption 59 and is located, mechanically pre-stressed, on at least one of a raised portion 60 each formed on the back 55 of the contact element support 44 and the opposite wall 45. In the present exemplary embodiment, the annularly-shaped spring element consists of a strip material and can be bent open towards the outside at its end sections 61 oriented towards the interruption 59. These end sections 61 are pressed together by means of an auxiliary tool, not shown, when the end section 27/3 on the connecting side of the sensor 27 is inserted; the connector plug 43 can be pushed on the end section 27/3 on the connecting side of the sensor 27 without damaging the coating of the contact elements 46 and the contact surfaces 36, because at that time the annularly-shaped spring element 47 no longer firmly rests on the contact element support 44 and the opposite wall 45. Instead of the above described end sections 61 of the annularly-shaped spring elements 47, which form a transverse gap, in another (not shown) embodiment of the spring element the end areas of the spring elements, which are provided with outwardly bent open end sections, can overlap. Following insertion of the sensor 27 into the connector plug 43, the entire auxiliary tool is removed again and by means of this the mechanical tension of the spring element 47 is allowed to act on the contact element support 44 and the opposite wall 45, as well as on the area of the sensor 27 enclosed by them. A second spring element 62 (shown in dash-dotted lines), which also has a transverse gap (not indicated) and can extend with its end sections (not indicated) as far as the end sections 61 of the first spring element 47, can be pushed coaxially on the strip-shaped spring element 47, if necessary, for increasing the spring effect. A crosswise extending protrusion 63 is formed on the backs 55 of the contact element support 44 and the opposite wall 45, which assists in the fixing and is used as a stop for the spring element 47, possibly also for the second spring element 62.

The connecting points 56 of the contact elements 46 and the connecting conductors 57 are each tightly enclosed in a through-hole 64 of a resilient, plug-like shaped element 65, which consists of a heat-resistant material, such as PTFE, and has an O-ring 66 of a more resilient material in an annular groove (not indicated) on its periphery; in this case the O-ring 66 coaxially extends with its outer diameter out of the surface of the shaped element 65. This shaped element 65 with the O-ring 66 is surrounded by the longitudinal section 67/1 on the connecting side of a metal sleeve 67 and pressed together, which causes a seal between the longitudinal section 67/1 of the metal sleeve and the shaped element 65 as well as a seal between the connecting conductors 57 and the shaped element 65; the O-ring 66 causes a particularly dependable seal between the shaped element 65 and the longitudinal section 67/1 of the metal sleeve. The metal sleeve 67 is pushed with its longitudinal section 67/1 on the gas measuring side on the first longitudinal section 16 of the metal housing 11 and fastened on it by welding or the like; the metal sleeve 67 is designed in the shape of steps and adapts itself by means of areas of different diameter to the actualities of the components of the gas measurement sensor 10 contained therein.

The connecting conductors 57 extending out of the shaped element 65 on the connecting side and having an insulation (not shown), together are conducted through an insulating sleeve 68.

For the purpose of amplification it should be mentioned that the term sensor element 38 particularly addresses gas measurement elements, at least one of which is disposed on the sensor 27, but that a plurality of them can also be applied to it; additionally, temperature sensors, moisture sensors, pressure sensors, and the like, can also be applied as further sensor elements to the sensor 27. Besides the at least one sensor element 38, layered heating elements are also often provided on the sensor 27, possibly layered resistors of defined characteristics can also be installed in the paths of the strip conductors 37.

Figure 7:
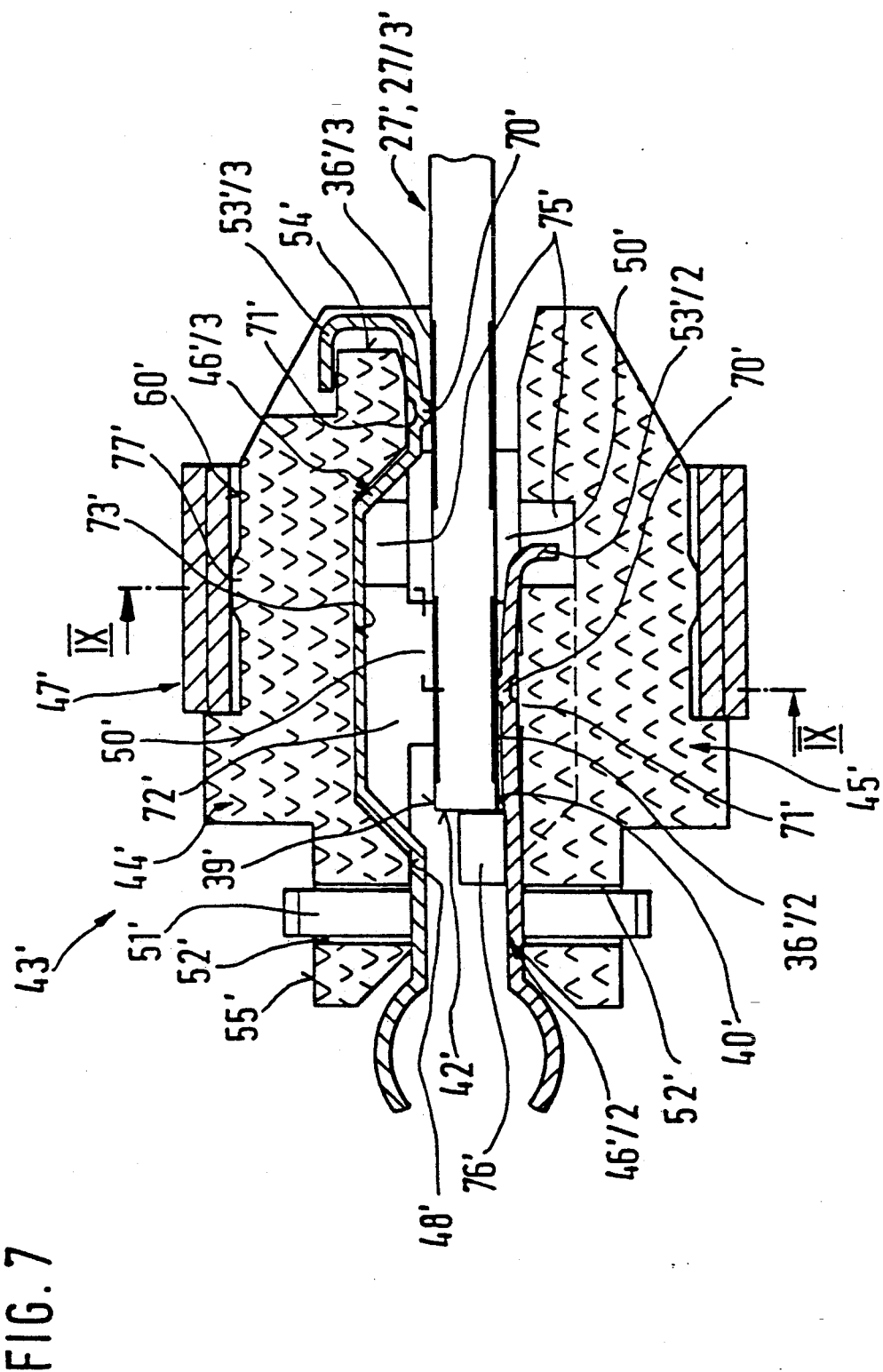

It has been shown in the further development of gas measurement sensors that sensors 27' with a plurality of sensor elements and possibly heating elements could be practical for the particularly precise regulation of exhaust gases and admixture of amounts of fuel or air for motor vehicle engines; such planar sensors 27' often require on the end section 27/3' on the connecting end not only two contact surfaces each on the two large areas 39' and 40', but also up to three contact surfaces 36' (see FIGS. 6 and 7). This contact surface 36' should have surfaces as large as possible for assured contact seating in associated connector plugs 43' (see FIGS. 7 to 9), but should still have sufficient distance between them for preventing shunts; in connection with this the connector plug 43' must be restricted in size in such a way that it continues to allow problem-free installation in the gas measurement sensor.

The three contact surfaces 36', applied in layers on a large area 39', 40' of such sensors 27', are arranged in such a way, that one of these contact surfaces 36'/1, 36'/2 is located close to the front face 42' on the connecting side and along a short side 41' of the sensor 27', and the third contact surface 36'/3 is applied on an imagined center line longitudinally extending between the other two contact surfaces 36'/1 and 36'/2, and this in the direction of the section on the gas measuring side of the sensor 27' and at a distance to the other two contact surfaces 36'/1, 36'/2. The width of the individual contact surfaces 36" preferably corresponds to approximately one third of the width of the sensor 27'; the distance between the contact surfaces 36'/1, 36'/2 near the front side and the third contact surface 36'/3 is, if possible, more than 2 mm. The materials used for such contact surfaces 36' are known and are not a subject of the instant patent application; in most cases the surface of such contact surfaces 36' is provided with an electrically-conducting, corrosion-resistant coating (for example of a noble metal). The conductor strips connected to the individual contact surfaces 36', which lead to the sensors or heating elements (not shown), are indicated by dash-dotted lines in FIG. 6.

Figure 8:
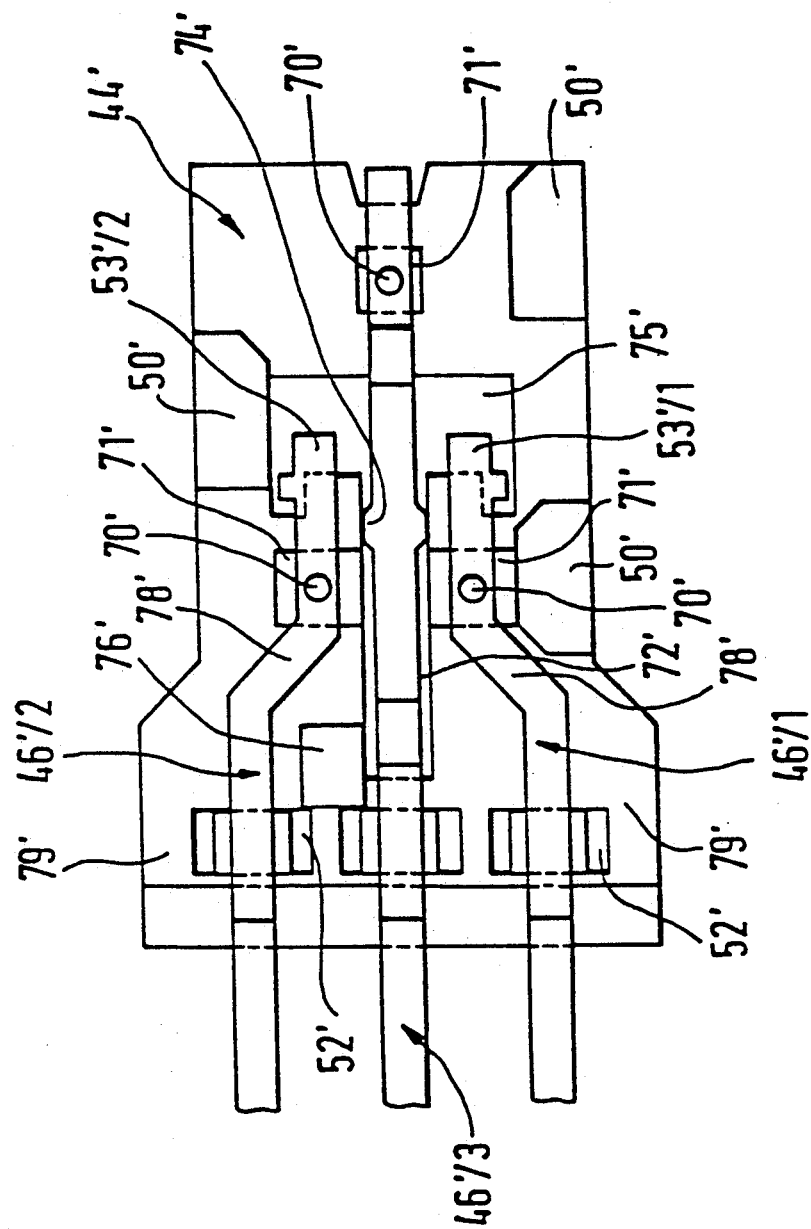
Figure 9:
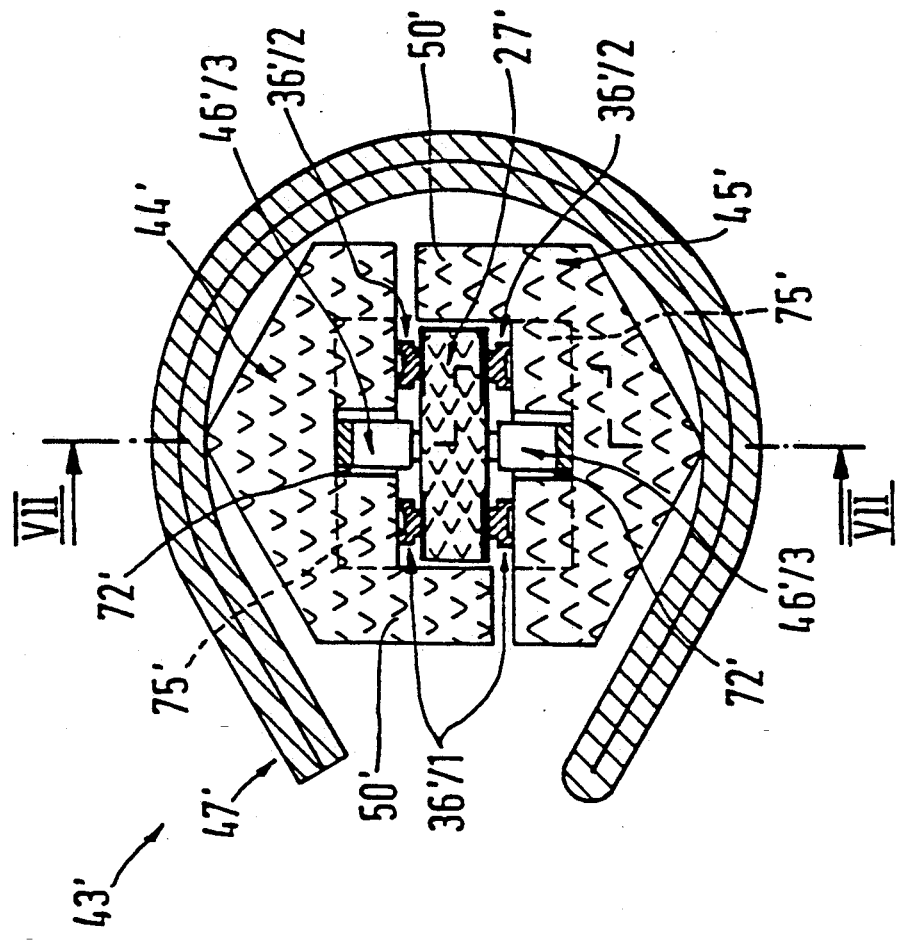

The connector plug 43' shown in FIGS. 7 to 9, intended for the above described sensor 27', corresponds in many of its features to the connector plug 43 shown in FIGS. 1, 3 to 5; this connector plug 43' also has a contact element support 44' and a opposite wall 45', each with contact elements 46', and an annularly-shaped spring element 47' which is under mechanical pre-stress, which presses the contact element support 44' and the opposite wall 45' with the respective contact elements 46' on the end section 27/3, on the connecting side of the sensor 27'.

The contact element support 44' and the opposite wall 45' consist of electrically insulating ceramic material and are of the same configuration; the embodiment of these two components 44' and 45' will therefore be described below by means of the example of the contact element support 44':

The front 48' of the contact element support 44' facing the sensor 27' has been provided with a plurality of formed-on guide bars 50', which are used for the lateral guidance of the end section 27/3' on the connecting side of the sensor 27' and for the fixation in the longitudinal direction of the contact element support 44' and the opposite wall 45'; the three guide bars 50' on the contact element support 44' selected by way of example are disposed on the lateral sections of the large area 39' and in this case offset in respect to each other in such a way, that they are in engagement with the corresponding guide bars 50' of the opposite wall 45'.

The front 48' of the contact element support 44' supports the three contact elements 46, which are disposed in the longitudinal direction and are laterally distant from each other and which, as in the exemplary embodiment in accordance with FIGS. 1 and 3, consist of essentially strip-shaped sheet metal, have an electrically well-conducting, corrosion-resistant coating (for example of gold or nickel of a few μm thickness) and which are also embodied on the connecting side in the same manner and fixed on the contact element support 44' by means of finger-shaped sheet metal sections 51'. Corresponding to the arrangement of the contact surfaces 36', described in connection with FIG. 6, on the end section 27/3' on the connecting side of the sensor 27', the contact sections 70' are disposed on these contact elements 46'; for assured seating, the contact sections 70' are embodied as wart-like protrusions, which can be produced by stamping, oriented in the direction towards the respective contact surface 36' of the sensor 27'. To increase the seating of the contact sections 70' on the said contact surfaces 36' of the sensor 27', it is possible to form additional flat protrusions 71' on the front 48' of the contact element support 44', instead of or in addition to these contact sections 70' of the contact elements 46', and this in each case below the contact sections 70' of the contact elements 46'.

In accordance with their associated contact surfaces 36'/1 to 36'/3, the contact elements 46' are designated as 46'/1 to 46'/3: accordingly, the contact elements 46'/1 and 46'/2 are the two lateral contact elements and the contact element 46'/3 is the contact element located on an imagined center line of the contact element support 44', somewhat on the gas measuring side. To achieve as great as possible a distance between the center contact element 36'/3 and the respective lateral contact elements 46'/1 and 46'/2, a longitudinal groove 72' is formed in the front 48' of the contact element support 44' below the center contact element 46'/3 in the area of closely located longitudinal sections of the lateral contact elements 46'/1 or 46'/2, and the affected longitudinal section of the center contact element 46'/3 is conducted near the bottom 73' of this longitudinal groove 72'; the transitions of this longitudinal groove 72' from the actual front 48' to its bottom 73' extend continuously. For the purpose of making the installation of such connector plugs 43' easier, the longitudinal groove 72' is wider than the prevailing strip width of the center contact element 46'/3, but the contact element 46'/3 is provided in this area on both sides with lateral fastening protrusions 74'. The end section 53'/3 on the gas measuring side of this contact element 46'/3 is bent around the front face 54' on the gas measuring side of the contact element support 44' as far as the back 55' of the latter.

The end sections 53'/1 or 53'/2 on the gas measuring side of the two lateral contact elements 46'/1 or 46'/2 already terminate in an area at a distance which lies between the lateral contact surfaces 36'/1 or 36'/2 and the center contact surface 36'/3 of the sensor 27'; because of this measure, a sufficient distance between the contact surfaces 36' is also achieved in this area. In a preferred embodiment, in which this distance has been further increased and which is even more easy to assemble, the end sections 53'/1 and 53'/2 on the gas measuring side extend into a cutout 75' which has been formed in the front 48' of the contact element support 44'; in a preferred way this cutout 75' is connected with the already described longitudinal groove 72', however, it is also possible to provide an individual cutout for each end section 53'/1 and 53'/2.

The sections on the connecting side of the two lateral contact elements 46'/1 and 46'/2 are each provided with a laterally outward pointing flange 78', which starts in the area of the longitudinal groove 72', and a widening 79' is formed on each one of the respective areas on the connecting side of the contact element support 44' and the opposite wall 45', in order to allow problem-free assembly with the required connecting conductors (see FIG. 1, position 57). The channels 52', used to fasten the contact elements 46'/1 and 46'/2, in the contact element support 44' and the opposite wall 45' are adapted in their position to the position of the finger-shaped sheet metal sections 51' of these flanged contact elements 46'/1 and 46'/2.

In this connector plug 43', the spring element 47' which in this example is formed from a one-piece, but two-layer strip, rests on a protrusion 77', which is also formed on the raised portions 60' on the back of the contact element support 44' and the opposite wall 45', in such a way the force exerted by the mechanically prestressed spring element 47' is evenly distributed on the six contact sections 70' of the connector plug 43'.

A protruding stop 76' is formed on the front 48' of the contact element support 44' for the longitudinal fixation of the sensor 27', on which the front 42' on the connecting side is intended to rest; such a stop can also be used on the opposite wall 45'.

In all other respects the connector plug 43' in accordance with FIGS. 7 to 9 corresponds to the connector plug 43 in accordance with FIGS. 1, 3 to 5. If it is intended to maintain such a connector plug 43, 43' in a particularly vibration-resistant manner inside the metal sleeve 67 of the gas measurement sensor 10 (see FIG. 1), it can be provided with a support sleeve (not shown) with an essentially U-shaped cross section, which has been bent from this spring steel sheet metal, encloses a large portion of the connector plug 43, 43' and has deviating bars, bent obliquely towards the exterior, which are supported on the interior of the metal sleeve 67 by means of their free ends which are subjected to mechanical pre-stress.

We claim:

1. A gas measurement sensor (10), especially for determining oxygen concentration in exhaust gases of internal combustion engines, with a pipe-shaped metal housing (11), which has means (12, 13, 14) for the sealing installation in a gas measurement line and contains in its longitudinal bore (19)

at least one longitudinal section of an axially extending sensor (27), which has an elongated, planar shape, is electrically insulated in respect to the metal housing (11), is divided by means of a seal disposed crosswise to the longitudinal bore (19) of the metal housing (11) into a section (27/1) on the gas measuring side and a section (27/2) on the connecting side, has at least one layered, electrically conductive contact surface (36) on the end section (27/3) of its section (27/2) on the connecting side on at least one of its large areas (39), which is in electrical connection via a strip conductor (37) with a sensor element (38) or a layered heating element and on which an electrical contact element (46) presses, which is part of a connector plug (43), which on the connecting side is in electrical contact on the connecting side with a connecting conductor (57) of the gas measurement sensor (10) and is disposed on an electrically insulating contact element support (44), also a part of the connector plug (43), where the connector plug (43) also has an electrically insulating opposite wall (45), which is disposed on the second large area (40) of the end section (27/3) of the section (27/2) on the connecting side of the sensor (27) and cooperates with the said connecting element support (44), characterized in that the contact element support (44) and the opposite wall (45) of the connector plug (43) are two components which are at a distance from each other, located parallel to the sensor (27) and electrically insulating, which each face a large area (39, 40) of the sensor (27) with a front (48, 49), where the front (48, 49) of the contact element support (44) supports the at least one contact element (46) which rests on an associated contact surface (36) on the sensor (27), and that an annularly-shaped spring element (47) is provided, which surrounds in a mechanically pre-stressed manner the contact element support (44) and the opposite wall (45) of the connector plug (43) in the area of the end section (27/3), disposed in the area between them both, of the section (27/2) on the connecting side of the sensor (27), and which has an interruption (59) in the peripheral extent.

2. A gas measurement sensor in accordance with claim 1,
characterized in that
the end sections (61) of the spring element (47) located close to the interruption (59) of the annularly-shaped spring element (47) point away from the connector plug (43).

3. A gas measurement sensor in accordance with claim 1,
characterized in that
the annularly-shaped spring element (47) consists of strip material.

4. A gas measurement sensor in accordance with claim 1,
characterized in that
such a second spring element (62), subject to mechanical pre-stressing, is coaxially disposed over the annularly-shaped spring element (47).

5. A gas measurement sensor in accordance with claim 1,
characterized in that
the contact element support (44) and the opposite wall (45) of the connector plug (43) each have on their backs (55) facing away from the sensor (27) at least one formed raised portion 60, on which the spring element (47) rests with its interior.

6. A gas measurement sensor in accordance with claim 1,
characterized in that
the contact element support (44) and/or the opposite wall (45) of the connector plug (43) have a formed protrusion (63) on their back (55) facing away from the sensor (27) for the longitudinal fixation of the spring element (47).

7. A gas measurement sensor in accordance with claim 1,
characterized in that
the contact element support (44) and/or the opposite wall (45) of the connector plug (43) have formed guide bars (50) on the front (48, 49) facing the sensor (27), each of which rests against the short sides (41) of the sensor.

8. A gas measurement sensor in accordance with claim 1,
characterized in that
the contact element support (44') and/or the opposite wall (45') of the connector plug (43') have a formed stop (76') on the front (48') facing the sensor (27'), which is used for the longitudinal fixation of the sensor (27').

9. A gas measurement sensor in accordance with claim 1,
characterized in that
the opposite wall (45) of the connector plug (27) is also provided on its front (49) facing the sensor (27) with at least one contact element (46), which cooperates with a contact surface (36) on the end section (27/3) of the section (27/2) on the connecting side of the sensor (27).

10. A gas measurement sensor in accordance with claim 1,
characterized in that
the contact elements are formed of strip-like sheet metal and have formed sheet metal sections (51) for their fixation on the contact element support (44) of the connector plug (43).

11. A gas measurement sensor in accordance with claim 1,
characterized in that
each contact element (46') has a raised contact section (70') pointing in the direction toward the associated contact surface (36') of the sensor (27').

12. A gas measurement sensor in accordance with claim 1,
characterized in that
the contact elements (46) of the connector plug (43) are provided with an electrically conducting, corrosion-resistant coating (for example of gold).

13. A gas measurement sensor in accordance with claim 10,
characterized in that
the contact elements (46) of the connector plug (43) extend out on the side of the connection between the contact element support (44) and the opposite wall (45) of the connector plug (43) and have connecting points (56) with associated connecting conductors (57) in this area.

14. A gas measurement sensor in accordance with claim 1,
characterized in that
the contact element support (44') and/or the opposite wall (45') of the connector plug (43') have, on the front (48') facing the sensor (27'), three essentially strip-shaped contact elements (46') at a lateral distance from each other, where one of these contact elements (46'/1, 46'/2) each is disposed on each longitudinal side of the contact element support (44') and/or the opposite wall (45'), and the respectively third contact element (46'/3) extends longitudinally between the two previously mentioned contact elements (46'/1, 46'/2), extends farther on the gas measuring side with its contact section (70') than the contact sections (70') of the two other contact elements (46'/1, 46'/2) and is partially guided in a longitudinal groove (72'), which is formed in the front (48') of the contact element support (44') and/or the opposite wall (45') and is at least located in the area of closely placed longitudinal sections of the contact elements (46'/1, 46'/2) disposed on the longitudinal sides of the contact element support (44') and or the opposite wall (45'), and that the end sections (53'/1, 53'/2) on the gas measuring side of the two contact elements (46'/1, 46'/2) located on the longitudinal sides of the contact element support (44') and/or the opposite wall (45') terminate at a distance from the respectively center contact surface (36'/3) of the sensor (27'), preferably extend into cutouts (75'), which are formed in the front (48') of the contact element support (44') and/or the opposite wall (45'), and that the planar sensor (27') has contact surfaces (36') on the section on the connecting side of its large areas (39' and/or 40') for at least one sensor element and possibly at least one heating element, which are at a distance from each other and in their position correspond to the position of the contact sections (70') of the connector plug (43').

15. A gas measurement sensor in accordance with claim 14, characterized in that
the contact element support (44') and the opposite wall (45') have a widening (79') in the longitudinal section on the connecting side and that the longitudinal sections on the connecting side of the respectively two laterally disposed contact elements (46'/1, 46'/2) follow this widening (79') via a flange (78') still located in the area of the longitudinal groove (72').

16. A gas measurement sensor in accordance with claim 14, characterized in that
raised portions (60') formed on the back (55') of the contact element support (44') and the opposite wall (45') each have a protrusion (77') which extends beyond the raised portions (60'), on which the annularly-shaped spring element (47') rests and which are disposed in such a way that the force exerted by the spring element (47') is evenly distributed over the contact sections (70').

17. A gas measurement sensor in accordance with claim 1, characterized in that
the front (48') of the contact element support (44') and or the opposite wall (45') has flat protrusions (71') below the adjoining contact sections (70') of the contact elements (46').

18. A gas measurement sensor in accordance with claim 1, characterized in that
the connecting points (56) of the contact elements (46) and of the connecting conductors (57) are each disposed in a through-hole (64) of a resilient, plug-like shaped element (65).

19. A gas measurement sensor in accordance with claim 18, characterized in that
resilient shaped element (65) is sealingly enclosed by a longitudinal section (67/1) of a metal sleeve (67) fastened on the connecting side on the metal housing (11), and that the connecting conductors (57) are also sealingly enclosed in the through-holes (64) of the shaped element (65).

* * * * *